United States Patent [19]

Southwick

[11] Patent Number: 4,739,076

[45] Date of Patent: Apr. 19, 1988

[54] SUBSTITUTED 3-PYRROLINE-2-ONE AMINO BLOCKING REAGENTS AND INTERMEDIATES THEREFOR

[76] Inventor: Philip L. Southwick, 36 Woodland Farms Rd., Pittsburgh, Pa. 15238

[21] Appl. No.: 712,140

[22] Filed: Mar. 15, 1985

[51] Int. Cl.[4] ............... C07D 207/28; C07D 207/273; C07D 403/12
[52] U.S. Cl. .................. 548/519; 548/531; 548/544; 548/550
[58] Field of Search ............ 548/550, 544, 546, 531, 548/519

[56] References Cited

U.S. PATENT DOCUMENTS

| | | | |
|---|---|---|---|
| 2,757,125 | 7/1956 | Mudrak | 548/531 |
| 2,824,110 | 2/1958 | Howard | 548/531 |
| 2,936,309 | 5/1960 | Bavley et al. | 548/531 |
| 3,714,175 | 1/1973 | Shigezane et al. | 548/550 |

FOREIGN PATENT DOCUMENTS

| | | | |
|---|---|---|---|
| 7141305 | 12/1969 | Japan | 548/544 |
| 57-183756 | 11/1982 | Japan | 548/544 |

OTHER PUBLICATIONS

Negri et al., Biochimica et Biophysica Acta, 579 (1979), pp. 31–39.
Southwick et al., J. Org. Chem., 39, pp. 3351–3359 (1974).
Southwick et al., J. Org. Chem. 34, 3275–3285 (1969).
Southwick et al., J. Org. Chem., 33, 2051–2056 (1968).
Pierce Bio–Research Products Technical Bulletin, vol. 5, revised May, 1984.

*Primary Examiner*—Glennon H. Hollrah
*Assistant Examiner*—David B. Springer
*Attorney, Agent, or Firm*—Andrew J. Cornelius; Alan P. Kass

[57] ABSTRACT

An amino blocking reagent, 1-isopropyl-3-ethoxy-4-nitro-2-oxo-3-pyrroline has been obtained. The new reagent is water soluble. It has yielded an N-protected glycine active ester with solubiity appropriate for reaction with both peptides and proteins. N-hydroxysuccinimide esters of N-i-NOPY- and N-c-NOPY-glycines were prepared. The N-hydroxysuccinimide active esters were produced by treatment with dicyclohexylcarbodimide (DCC) and N-hydroxysuccinimide in tetrahydrofuran (THF). The new reagents for glycine attachment are stable crystalline compounds. These active esters were used to attach glycine residues to a dipeptide and a protein by the salt-coupling procedure.

7 Claims, No Drawings

SUBSTITUTED 3-PYRROLINE-2-ONE AMINO BLOCKING REAGENTS AND INTERMEDIATES THEREFOR

BACKGROUND OF THE INVENTION

Southwick, P. L., et al., J. Org. Chem., 39, 3351 (1974), described the preparation of the reactive nitro enol ether 1-cyclohexyl-3-ethoxyl-4-nitro-2-oxo-3-pyrroline(6a), as well as some applications of this compound as a reagent for the introduction of a reversible amino protecting group (the 1-cyclohexyl-4-nitro-2-oxo-3-pyrrolin-3-yl or "c-NOPY" group where "NOPY" stands for 4-nitro-2-oxo -pyrrolin-3-yl). Applications of the NOPY blocking group in simple examples of peptide synthesis and protein modification have been described in Southwick, P. L. ibid. and Negri, D. J.; Southwick, P. L.; Brown, W. E., Biochem. Biophys. Acta, 579, 31 (1979).

Advantages of the NOPY-group are its ease of introduction (short reaction times in partially aqueous media at ca. 25° C. and pH 7.5-9), ease of removal (treatment with ammonia or aqueous base at ca. 25° C.), and the convenience with which it is monitored through its high absorptivity at 367-385 nm and visibility on thin-layer chromatography plates with 254-nm fluorescent indicator.

For many applications, however, it would be useful to have a new blocking reagent that would be more water soluble and which would introduce a blocking group that adds only minimally to the hydrophobic character of a resulting protected amino acid or peptide derivative. A reagent of the NOPY type with cyclohexyl replaced by a smaller group was thought likely to have such properties.

The reagent 9-fluorenylmethyl chloroformate also introduces a blocking group which is removable under mild alkaline conditions. It is, however, water-insoluble, as is a previously introduced congener of our new reagent. The presence of the blocking group introduced by the 9-fluorenylmethyl chloroformate reagent is less readily determined spectroscopically.

U.S. Pat. No. 4,460,501 also discloses blocking groups for protecting amine groups.

SUMMARY OF THE INVENTION

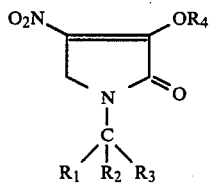

A new reagent is a member of a family of compounds in which $R_1$, $R_2$ and $R_3$ are alkyl, groups having 1-4 carbon atoms or hydrogen, and $R_4$ is an alkyl group having 1-4 carbon atoms. The reagent, in which $R_1$ and $R_2$ are methyl, $R_3$ is hydrogen, and $R_4$ is ethyl, has been found to meet the foregoing expectations. The new reagent is water soluble and has yielded an N-protected glycine active ester with solubility appropriate for reaction with both peptides and proteins. Since the acronym NOPYE (for nitrooxopyrrolinyl ethyl ether) had been applied to compound 6a; the new isopropyl-containing reagent will be called "i-NOPYE." The derived NOPY groups will similarly be distinguished as "c-NOPY" and "i-NOPY". NOPY will with the 1-substituent constituted of groups $R_1$ $R_2$ and $R_3$ as above specified.

The new nitro enol ether showed a solubility in water in excess of 10 mg/mL at 25° C. Its solubility is more than sufficient for use in purely aqueous solutions to block amino functions of proteins. Proteins such as lysozyme and chymotrypsin, for example, underwent extensive reaction in water or 6M guanidine hydrochloride with the i-NOPYE reagent (6b) under conditions previously used with the c-NOPYE reagent (6a), but without the need to add acetone or any other miscible organic solvent.

Synthesis of the i-NOPYE Reagent (6b). A synthetic sequence based on a different type of starting material as compared to the c-NOPYE reagent was needed to obtain satisfactory and reproducible yields of the i-NOPYE reagent. Conversion of the enol of 3-carbethoxy-1-isopropyl-2,3-dioxopyrrolidine into the final intermediate, 3-ethoxy-1-isopropyl-2-oxo-3-pyrroline-4-carboxylic acid (4b) was otherwise attended by formation of excessive amounts of dark-colored byproducts in the saponification step.

In accordance with another feature of the invention, an alternative synthetic route devised to circumvent this problem is shown in Scheme I. Starting from the readily available enolic 4,5-dicarbethoxy-1-isopropyl-2,3-dioxopyrrolidine (1b), rather than the corresponding 4-monocarbethoxy derivative, ethylation of the enolic hydroxyl was carried out with triethyl orthoformate. The resulting crude enol ether (2b) was not purified but was saponified directly to yield a solution containing disodium salt (3b), which upon acidification underwent conversion to the diacid (4b), followed by rapid decarboxylation with precipitation of the enol ether monocarboxylic acid (5b). Direct nitration of (5b) accompanied by decarboxylation then produced the nitro enol ether (6b) as in the synthesis of 6a.

The new sequence gave reliable yields of 60% to 65%. This transformation may be carried out in a one-pot process. It has since been found that the sequence of Scheme I, starting with the 4,5-diester, also gives more reliable results in the preparation of the c-NOPYE intermediate than did the previously published procedures starting from the 4-mono ester. The 5-ester group serves as a removable blocking group against side reactions.

The c-NOPY- and i-NOPY-Gly-OSu Glycylating Reagents 8a and 8b). Since NOPY groups, like peptides and proteins themselves, have the character of amides, it was anticipated that solvent systems which are known to dissolve many proteins and/or polypeptides could be adjusted to dissolve N-NOPY amino acids and properly selected acylating derivatives of such protected amino acids. Such solubility properties should facilitate use of these derivatives for attachment of amino acid residues to peptides or proteins by the salt-coupling technique, in which free carboxylate groups of the substrate are not blocked, and the coupling reaction can be carried out in aqueous or mixed organic-aqueous solutions. The c- or i-NOPY-protected glycines were obtained by treatment of glycine at ca. 25° C. with a NOPYE reagent in water or a water-acetonitrile mixture at pH 8-9 (Scheme II). A wide variety of such amino acid compounds may similarly be prepared.

These compounds have the following formula:

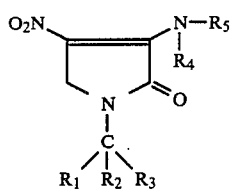

where $R_1$, $R_2$ and $R_3$ are alkyl, cycloalkyl, aryl, aralkyl or hydrogen, and $R_4$ and $R_5$ are the remainder of the structure of a natural or synthetic amino acid, an amine, H, a peptide or a polypeptide.

N-hydroxysuccinimide esters of N-i-NOPY- and N-c-NOPY-Gly were then prepared (8a,b). These N-hydroxysuccinimide active esters were produced from these products by treatment with dicyclohexylcarbodimide (DCC) and N-hydroxysuccinimide in tetrahydrofuran (THF). The new reagents for glycine attachment (8a,b) are stable crystalline compounds.

These compounds have the formula

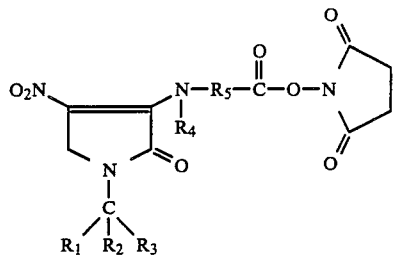

where $R_1$, $R_2$ and $R_3$ are alkyl, cycloalkyl, aryl, aralkyl or hydrogen, and $R_4$ and $R_5$ are the remainder of the structure of a natural or synthetic amino acid, a peptide, H or a polypeptide.

Specific examples of such compounds include the N-hydroxysuccinimide ester of N-(1-cyclohexyl-4-nitro-2-oxo-3-pyrroline-3-yl)glycine and the N-hydroxysuccinimide ester of N-(1-isopropyl-4-nitro-2-oxo-3-pyrroline-3-yl)glycine.

These active esters were used to attach amino acids residues to a dipeptide and a protein by the salt-coupling procedure.

As alternatives to the imide esters, ortho and para nitrophenyl, pentachlorophenyl and pentafluorophenyl may be reacted with the NOPY groups. The same reactive conditions may be used as with the production of the above described imide esters.

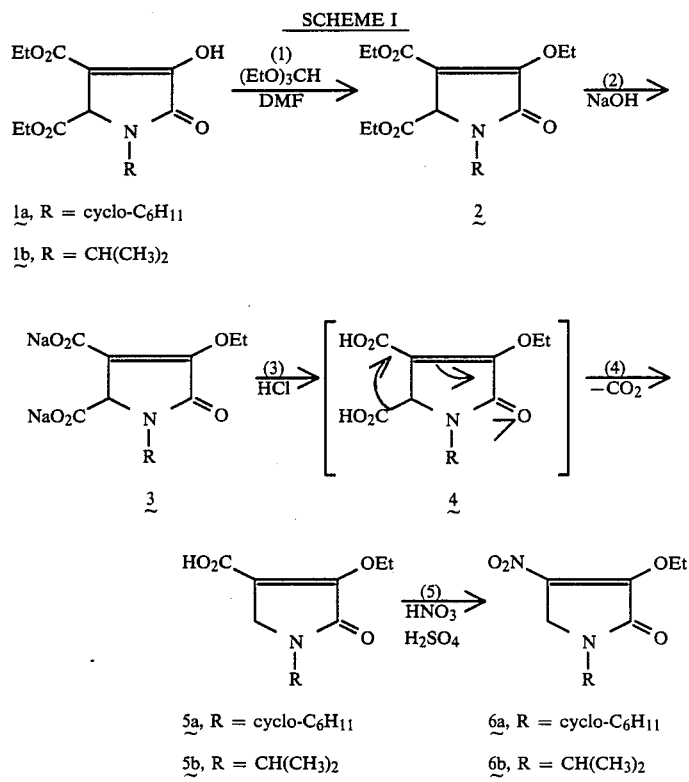

SCHEME I

SCHEME II

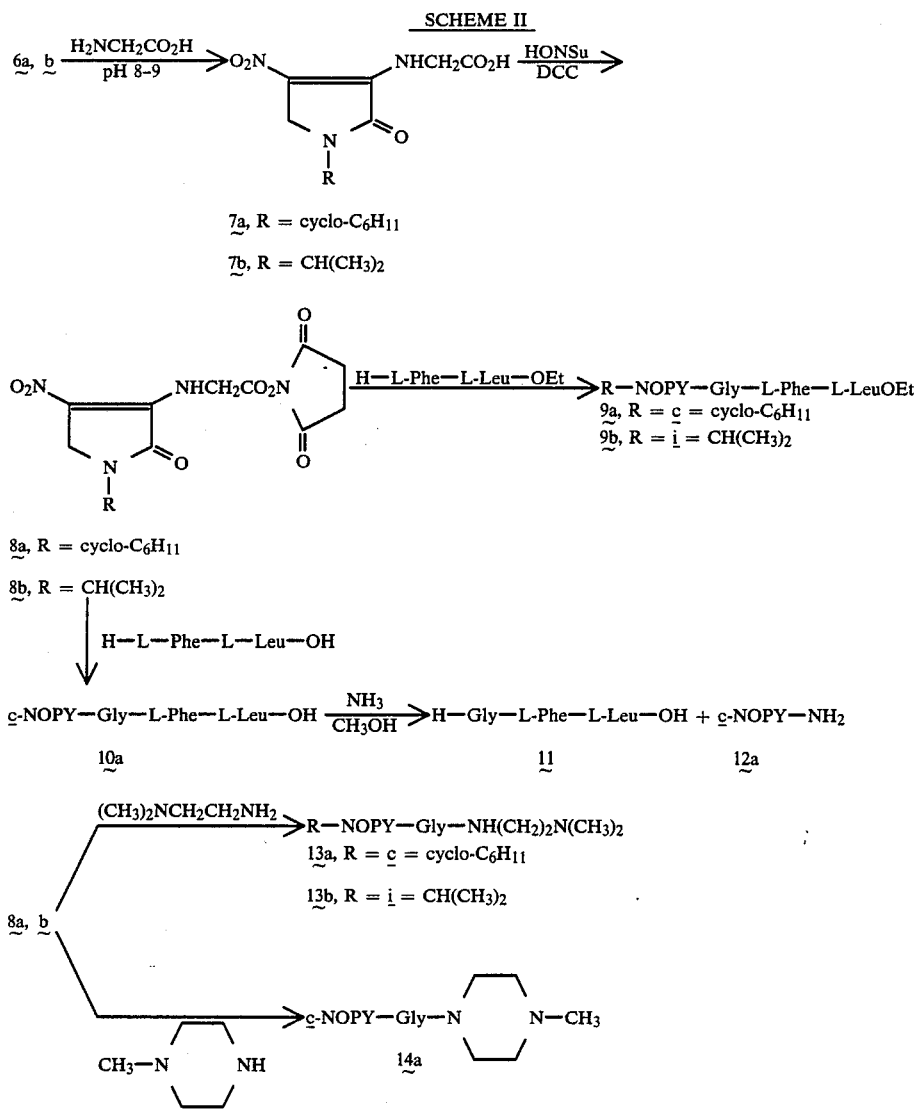

These compounds have the formula

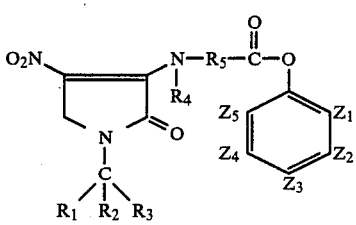

where $R_1$, $R_2$ and $R_3$ are as defined above, $R_4$ and $R_5$ are the remainder of the structure of a natural or synthetic amino acid, a peptide or a polypeptide and where Z=hydrogen, chloro fluoro or nitro; for example, where $Z_1$—$NO_2$ and $Z_2$-$Z_5$=hydrogen or where $Z_3$=$NO_2$ and $Z_1$, $Z_2$, $Z_4$ and $Z_5$=hydrogen.

Preferably the aromatic ring is o-nitrophenyl, -p-nitrophenyl, pentachlorophenyl or pentafluorophenyl.

Amino acid residues were added to both the dipeptide L-phenylalanyl-L-leucine (H-L-Phe-L-Leu-OH) and its ethyl ester (H-L-Phe-L-Leu-OEt) by use of 8a and/or 8b. Coupling with the ethyl ester was conducted in THF, whereas coupling with H-L-Phe-L-Leu-OH itself was carried out by the salt-coupling technique in a solvent mixture of water, acetonitrile, and dimethylformamide (DMF) in the presence of potassium carbonate. The product of the latter coupling procedure was a tripeptide c-NOPY-L-Gly-L-Phe-L-Leu-OH (10a).

Thus, a wide variety of NOPY derivatives of mono-, di-, tri- and polypeptides can be obtained generally of the formula

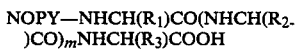

and

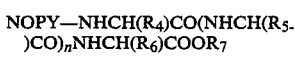

Where $R_1$ through $R_6$ are H or the remainder of the structure of a natural or synthetic amino acids, and $R_7$ is lower alkyl or aralkyl. These products may be deblocked by brief treatment with methanolic ammonia to yield the free tripeptide (11).

An advantage inherent in the use of NOPY protecting groups lies in the fact that the available ammonia deblocking procedure can yield deblocked peptide directly in the free form rather than as a hydrochloride or other salt. The heterocyclic amino derivatives c- or i-NOPY-NH$_2$ (12), formed from the NOPY groups in ammonia deblocking, are non basic compounds that are readily removed by virtue of their solubility in organic solvents such as acetone or methylene chloride.

DESCRIPTION OF PREFERRED EMBODIMENTS AND EXAMPLES

A. APPARATUS AND TECHNIQUE

Spectrophotometers used for the reported measurement were a Perkin-Elmer Model 237B (infrared spectra) and Perkin-Elmer Model 202 (ultraviolet spectra). Infrared bands in the range 2.5–9.25 μm are reported. Nuclear magnetic resonance measurements were made with a Perkin-Elmer Model R-24 instrument (60 MHz) and a Bruker Model WM-300 instrument (300 MHz). Optical rotations were measured with a Perkin-Elmer Model 241 polarimeter. Amino acid analyses were performed on a Durrum D-500 amino acid analyzer. Samples for analysis were hydrolyzed in 6N HCl for 24 h at 110° C. in vacuo. Elemental analyses were by M-H-W Laboratories, Phoenix, Ariz. Thin-layer chromatography (TLC) on NOPY derivatives was carried out on Baker-flex silica 1B2-F sheets.

B. DESCRIPTION OF PREFERRED EMBODIMENTS AND EXAMPLES

EXAMPLE I

Preparation of
3-Ethoxy-1-isopropyl-2-oxo-3-pyrroline-4-carboxylic Acid (5b)

A solution prepared from 22 g (0.078 mol) of 1b, 55 mL (48 g, 0.33 mol) of triethyl orthoformate, 75 mL of DMF, and 0.5 g of p-toluenesulfonic acid hydrate was heated and stirred with a magnetic stirrer in an insulated distillation apparatus of the Claisen type. The voltage to the heating mantle was regulated so that the temperature of the distilling vapors leaving the flask (mainly EtOH and HCO$_2$Et) did not exceed 78° C., while the temperature registered by a thermometer placed in the boiling liquid rose gradually to 150° C. After ca. 3 h at a constant voltage setting, the distillation almost ceased and the temperature at the still head fell to 40°–45° C. The reaction mixture was then transferred to a rotary evaporator for the removal of the DMF and unused triethyl orthoformate under reduced pressure.

The residual thick oil was dissolved in a mixture prepared from 100 mL of EtOH, 100 mL of H$_2$O, and 16 g of NaOH and heated on a steam bath for 45 min. under a reflux condenser. The solution was transferred to a rotary evaporator, and the ethanol and water were removed under reduced pressure. The residue was dissolved in 100 mL of water, cooled in an ice bath, and acidified to pH 2 with hydrochloric acid. The product separated as tan crystals; mp ca. 127° C., yield 10 g (60%). A sample was recrystallized from CH$_2$Cl$_2$-ether or successively from EtOH and from EtOAc to give a white product: mp 131°–133° C.; $^1$H NMR (CDCl$_3$) δ11.05 (s, 1H, CO$_2$H), 4.99–4.25 (q+septet, 3H, overlap of OCH$_2$CH$_3$ and NCH(CH$_3$)$_2$, J=7 Hz), 4.00 (s, 2H, CH$_2$ of pyrroline), 1.54–1.20 (t+d, 9H, overlap of CH$_2$CH$_3$ and NCH(CH$_3$)$_2$, J=7 Hz); UV (95% EtOH) 252 nm (ε13400); IR (Nujol) 3.75, 3.85, 4.05, 5.90, 6.02, 6.15, 6.91, 7.06, 7.19, 7.29, 7.50, 7.98, 8.25, 8.55, 8.75, 9.03 μm.

Anal. Calcd for C$_{10}$H$_{15}$NO$_4$: C, 56.32; H, 7.09; N, 6.57. Found: C, 56.25; H, 7.16; N, 6.62.

EXAMPLE II

Preparation of Precursor of NOPYE reagent
1-Cyclohexyl-3-ethoxy-2-oxo-3-pyrroline-4-carboxylic Acid (5a)

The 1-cyclohexyl derivative 5a was prepared in the current investigation from the enolic 4,5-dicarbethoxy-1-cyclohexyl-2,3-dioxopyrrolidine (1a) by a similar procedure conducted on nearly the same scale (ca. 0.088 mol of 1a used in many experiments). Both the 4,5-dicarbethoxy derivative 1a and the 4,5-dimethoxy derivative (mp 160° C.) have been used as starting materials with similar results. The procedure was identical with that described above for 5b, except that it was not necessary to conduct an evaporation to remove ethanol from the saponification mixture, which was instead filtered and poured into a mixture of 200 mL of ice and 50 mL of ethanol before acidification to precipitate the product. The typical yield of 5a, mp 154°–155° C., from 0.088 mol of starting material was 16 g (72%), a result equivalent to the best obtained from the more complex two-step conversion of 4-carbethoxy-1-cyclohexyl-2,3-dioxopyrrolidine described previously.

EXAMPLE III

Preparation of NOPYE reagent
1-Isopropyl-4-nitro-3-ethoxy-2-oxo-3-pyrroline (i-NOPYE, 6b)

3-Ethoxy-1-isopropyl-2-oxo-3-pyrroline-4-carboxylic acid (5b, 8 g, 0.0376 mol) in powdered form was added in small portions through a seive to a stirred mixture of 70 mL of concentrated sulfuric acid and 4.7 mL of white fuming nitric acid (90%) that had been cooled to −5° C. prior to the start of the addition of 5b. The rate of addition of 5b was controlled so as to keep the temperature of the reaction mixture from rising above −3° C. and to minimize accumulation of undissolved lumps of starting material in the mixture. Stirring was continued for 3 h at −3° C. Effervescence caused by carbon dioxide evolution began after the mixture had been stirred for a few minutes and virtually ceased after an hour of two. When the mixture was poured slowly into a stirred suspension of 1 L of crushed ice, the product separated as a white crystalline precipitate. It was collected by filtration as soon as the ice was melted and washed on the filter with a small amount of cold water. The yield was 4.9 g (61%), mp 47°–47° C. Recrystallization from acetone or benzene and petroleum ether (bp 30°–60° C.) raised the melting point to 49°–50° C.: $^1$H NMR (CDCl$_3$) δ4.90 (q, 2H, OCH$_2$CH$_3$, J=7 Hz), 4.40 (septet, 1H, NCH(CH$_3$)$_2$, J=7 Hz), 4.15 (s, 2H, CH$_2$ of pyrroline), 1.55–1.20 (t+d, 9H, overlap of —OCH$_2$CH$_c$ and NCH(CH$_3$)$_2$, J=7 Hz); IR (thin film) 3.34, 3.39, 3.47, 5.87, 6.08, 6.69, 6.92, 7.17, 7.3, 7.30, 7.38, 7.67, 7.93, 8.10, 8.40, 8.55, 8.75, 8.87, 9.05 μm; UV (95% EtOH) 293 nm (ε9800).

Anal. Calcd for C$_9$H$_{14}$O$_4$N$_2$: C, 50.46; H, 6.59; N, 13.08. Found: C, 50.32; N, 6.46; N, 13.12.

EXAMPLE IV

Preparation of NOPYE Protected Amino Acid

N-(1-Isopropyl-4-nitro-2-oxo-3-pyrrolin-3-yl)glycine (7b, i-NOPY-Gly-OH)

Glycine (0.75 g, 0.01 mol) and 0.7 g (0.005 mol) of potassium carbonate were dissolved in 10 mL of water. A solution of 1.07 g (0.005 mol) of i-NOPYE (6b) in 5 mL of acetonitrile was added, and the mixture was stirred for 1 h at room temperature and then acidified to pH 2 by addition of 6N hydrochloric acid to the stirred mixture. Stirring was continued while the mixture was cooled in an ice bath to complete separation of the product as a finely divided crystalline precipitate, which was collected by filtration. The yield was 1.0 g (82%); mp 180°–185° C. Recrystallization from acetic acid-water gave pale yellow crystals; mp 185°–185° C.; $^1$H NMR (CDCl$_3$ and CF$_3$CO$_2$H) δ8.35 (br, 1H, NH), 4.79 (d, 2H, CH$_2$ of Gly, J=6 Hz), 4.41 (septet, 1H, NCH(CH$_3$)$_2$, J=7 Hz, partly obscured by adjacent signals), 4.31 (s, 2H, CH$_2$ of pyrroline ring), 1.34 (d, 6H), NCH(CH$_3$), J=7 Hz); IR (Nujol) 3.01, 5.85, 5.90, 6.06, 6.92, 7.05, 7.25, 7.90, 8.20, 8.90, 9.08 μm; UV (EtOH) 262 nm (ε3900), 369 (ε14440).

Anal. Calcd for C$_9$H$_{13}$N$_3$O$_5$: C, 44.44; H, 5.39; N, 17.28. Found: H, 5.59; N, 16.95.

EXAMPLE V

Preparation of an Active Ester of NOPYE Amino Acid

N-Hydroxysuccinimide Ester of N-(1-Cyclohexyl-4-nitro-2-oxo-3-pyrrolin-3-yl)glycine (8a, c-NOPY-Gly-OSu)

To a solution of 0.432 g (3.75 mmol) of N-hydroxysuccinimide (HOSu) and 0.71 g (2.5 mmol) of N-(c-NOPY)-Gly (7a) in 10 mL of tetrahydrofuran (THF) was added 0.6 g (2.9 mmol) of di-dyclohexylcarbodiimide (DDC), and the mixture was stirred overnight at room temperature. The crystalline precipitate that separated was removed by filtration and extracted with 20 mL of boiling THF to recover a quantity of the N-hydroxysuccinimide ester that separated in the precipitate along with N,N'-dicyclohexylurea (DCU). After cooling and filtering to remove DCU, the extract was combined with the first filtrate, and the solution was taken to dryness under reduced pressure in a rotary evaporator. The residue was treated with 5 mL of hot methylene chloride, and the resulting solution was diluted with 10 mL of petroleum ether (bp 30°–60° C.). A light tan crystalline precipitate separated; mp 180°–181° C. The yield was 0.723 g (76%). Recrystallization from methylene chloride-petroleum ether (bp 30°–60° C.) raised the melting point to 192°–194° C.; IR (Nujol) 3.04, 5.42, 5.60, 5.76, 5.92, 6.06, 6.96, 7.03, 7.15, 7.28, 7.81, 7.93, 8.05, 8.23, 8.40, 9.23 μm.

Anal. Calcd for C$_{16}$H$_{20}$N$_4$O$_7$: C, 50.52; H, 5.30; N, 14.73. Found: C, 50.42; H, 5.39; N, 14.58.

EXAMPLE VI

Synthesis of an Active Ester

N-Hydroxysuccinimide Ester of N-(1-Isopropyl-4-nitro-2-oxo-3-pyrrolin-3-yl)glycine (8b, i-NOPY-Gly-OSu)

To a filtered solution of 1.15 g (10 mmol) of HOSu and 2.2 g (9 mmol) of N-(i-NOPY)-Gly (7b) in 40 mL of THF was added a solution of 2.06 g (10 mmol) of DCC in 10 mL of THF, and the mixture was kept at room temperature overnight. After removal of the precipitated DCU by filtration, the filtrate was taken to dryness at reduced pressure in a rotary evaporator. The solid residue was dissolved in 10 mL of THF and crystallization was induced by addition of 20 mL of petroleum ether (bp 30°–60° C.). The yield was 2.4 g (78%) of pale yellow crystals, mp 163°–165° C. An analytical sample of the same melting point was obtained by recrystallization from the same solvents: $^1$H NMR (CDCl$_3$) and CF$_3$CO$_2$H) δ8.3 (br, 1H, N—H), 5.13 (d, 2H, CH$_2$ of Gly, J=7 Hz), 4.4 (septet, 1H, NCH(CH$_3$)$_2$, J=7 Hz, overlapped by adjacent signal at 4.21), 4.21 (s, 2H, CH$_2$ of pyrroline ring), 2.95 (s, 4H, CH$_2$ of succinimide ring), 1.36 (d, 6H, NCH(CH$_3$)$_2$, J=7 Hz); IR (Nujol) 2.98, 5.50, 5.60, 5.77, 5.89, 6.04, 6.07, 6.91, 7.03, 7.18, 7.28, 7.89, 7.92, 8.13, 8.56, 9.25 μm; UV (95% EtOH) 367 nm (ε15400).

Anal. Calcd for C$_{13}$H$_{16}$O$_7$N$_4$: C, 45.88; H, 4.94; N, 16.47. Found: C, 45.75; H, 4.94; N, 16.20.

EXAMPLE VII

Synthesis of NOPY Protected Tripeptide Ester

N-(c-NOPY)-glycyl-L-phenylalanyl-L-leucine Ethyl Ester (9a, c-NOPY-Gly-L-Phe-L-Leu-OEt)

The procedure was the same as that described above for i-NOPY-Gly-L-Phe-L-Leu-OEt (9b). A 1-mmol quantity of H-L-Phe-Leu-OEt.HCl treated with 2 mmol of 8a in this manner yielded a yellow solid when the final methylene chloride solution was evaporated. The product was dissolved in methylene chloride and crystallization induced by addition of an equal volume of ether. Pale yellow crystals were obtained; mp 212°–213° C., yield 0.40 g (70%). Recrystallization from ethanol gave nearly white crystals; mp 222°–223° C., homogeneous by TLC, R$_f$ 0.82 (CHCl$_3$:CH$_2$Cl$_2$:CH$_3$OH, 5:5:1); UV (EtOH) 369 nm (ε15700); IR (Nujol) 2.93, 3.09, 5.74, 5.84, 5.93, 6.09, 6.52, 6.96, 7.21, 7.29, 7.41, 7.91, 7.98, 8.31, 9.10 μm; [α]$^{25}_{589}$−5.77° (c 1.08, HOAc).

Anal. Calcd for C$_{29}$H$_{41}$N$_5$O$_7$.½H$_2$O; C, 59.98; H, 7.29; N, 12.06. Found: C, 59.84; H, 7.25; N, 12.11.

EXAMPLE VIII

Synthesis of NOPY Protected Tripeptide

N-(c-NOPY)-glycyl-L-phenylalanyl-L-leucine (10, c-NOPY-Gly-L-Phe-L-Leu-OH)

To a solution of 0.570 g (1.5 mmol) of 8a in 10 mL of acetonitrile and 2 mL of DMF was added a solutin of 0.278 g (1 mmol) of L-phenylalanyl-L-leucine (Sigma) and 0.138 g (1 mmol) of potassium carbonate in 5 mL of water. After the mixture had been stirred at room temperature for 2 h, 0.11 mL of N-methylpiperazine was added and stirring was continued for 30 minutes. The solutoin was acidified to pH 2 with 6N hydrochloric acid, and 15 mL of water was added. Scratching of the walls of the flask induced crystallization of the product as light-yellow needles, partial melting (transition) 132°–136° C., final melting with decomposition 165°–175° C.; yield 0.389 g (71%); homogeneous by TLC, R$_f$ 0.32 (CHCl$_3$:CH$_2$Cl$_2$:CH$_3$OH:HOAc, 36:4:2:1); IR (Nujol) 2.94, 3.02, 5.78, 5.84, 6.08, 6.52, 6.93, 7.22, 7.28, 7.40, 7.89, 7.97, 8.32, 8.72, 9.12 μm; UV (EtOH) 369 nm (ε14700); [α]$^{25}_{589}$−4.4° (c 1.03, HOAc).

Anal. Calcd for C$_{27}$H$_{37}$H$_5$)$_7$: C, 59.65; H, 6.86; N, 12.89. Found: C, 59.74; H, 7.00, N, 12.63. Amino aicd analysis: Gly, 1.01; Phe, 0.99; Leu, 1.00.

EXAMPLE IX

Deblocking of NOPY Group to give un-blocked Tripeptide Glycyl-L-phenylalanyl-L-leucine (11, H-Gly-L-Phe-L-Leu-OH)

c-NOPY-Gly-Phe-Leu-OH (10, 0.545 g, 1 mmol) was dissolved in 40 mL of methanol, which had been saturated with anhydrous ammonia. The solution was stirred for 2 h at room temperature, and then concentrated to volume of ca. 5 mL under reduced pressure in a rotary evaporator. Pyridine (20 mL) was added, and the solution was again concentrated to ca. 5 mL. Upon addition of a small amount of acetone and 30 mL of ether, the product separated as a light buff-colored precipitate and was collected by filtration, yield 0.297 g. Colored impurities were removed by extraction with 5 mL of hot ethanol to yield 0.187 g (56%) of white product, mp 220°-223° C. The tripeptide separated as clumps of slender white needles, mp 225°-227° C. dec, when its solutions in ammonium hydroxide were maintained for a time under reduced pressure. The product was homogeneous by TLC, $R_f$ 0.44 (1-butanol:acetic acid:water, 10:1:3) on Analtech silica gel G plates (lit. $R_f$ 0.45): IR (Nujol) 3.03, 6.00, 6.04, 6.13, 6.47, 7.26. 7.48, 7.58, 7.69, 7.93, 8.10, 8.73, $\mu$m; $[\alpha]^{25}_{589}$ −12.9° (c 1.06, HOAc) [lit. $[\alpha]^{25}_{589}$ −12.5° (c 1.04, HOAc).

Anal. Calcd for $C_{17}H_{25}N_3O_4$: C, 60.87, H, 7.51; N, 12.53. Found: C, 60.68; H, 7.80; N, 12.53.

EXAMPLE X

Synthesis of NOPY Protected Tripeptide Ester N-(i-NOPY)-glycyl-L-phenylalanyl-L-leucine Ethyl Ester (9b, i-NOPY-Gly-L-Phe-L-Leu-OEt)

To a solution of 0.342 g (1 mmol) of L-phenylalanyl-L-leucine ethyl ester hydrochloride and 0.23 mL of N-methylmorpholine in 10 mL of THF was added 8b (0.64 g; 1.9 mmol) with stirring after the solution had been cooled in an ice bath. Cooling was continued for 30 min., and the the mixture was allowed to warm to room temperature and stirring was continued overnight. After a small amount of insoluble material had been removed by filtration, the filtrate was concentrated under reduced pressure in a rotary evaporator. The residual oil was dissolved in 20 mL of methylene chloride, and 0.08 mL of N,N-dimethylethylenediamine was added. The mixture was stirred for 10 min. at room temperature, then extracted twice with 15-mL portions of 2N hydrochloride acid, once with 15 mL of 2% sodium bicarbonate, and once with 15 mL of water. Concentration of the mehtylene chloride solution under reduced pressure in a rotary evaporator left an orange-red oil, which yielded white crystals when mixed with ca. 5 mL of absolute ethanol. The yield was 0.24 g (45%): mp 220°-222° C.; homogeneous by TLC, $R_f$ 0.79 ($CHCl_3:CH_2Cl_2:CH_3OH$, 5:5:1); $^1H$ NMR ($CDCl_3$) $\delta$8.43 (br, 1H NH of Gly), 7.29-7.19 (m, 5H, Ph of Phe), 4.76-4.69 (q, 1H, $\alpha$-H of Phe, J=7 Hz), 4.60-4.57 (d, 2H, $CH_2$ of Gly, J=6.5 Hz), 4.53-4.39 (m, 2H, overlap of $\alpha$-H of Leu with $NCH(CH_3)_2$), 4.19-4.12 (s+q, 4H, overlap of $CH_2$ of pyrroline and $-OCH_2CH_3$), 3.13-3.08 (m, 2H $CH_2$ of Phe) 1.71 (s, 2H, NH of Phe and Leu), 1.61-1.45 (m, 3H, $-CH_2CH(CH_3)_2$ of Leu), 1.29-1.23 (t+d, 9H, overlap of $-OCH_2CH_3$ and $NCH(CH_3)_2$), 0.90-0.88 (d, 5H, $-CH(CH_3)_2$ of Leu, J=6 Hz); UV (EtOH) 369 nm ($\epsilon$13700); $[\alpha]^{25}_{589}$ −2.8° (c 1.06, HOAc).

Anal. Calcd for $C_{26}H_{37}O_7N_5 \cdot H_2O$: C, 56.81; H, 7.15; N, 12.75. Found: C, 56.78, 57.03; H, 7.02, 6.95; N, 12.60, 12.51. Aminoacid analysis: Gly, 0.95; Phe, 1.00; Leu; 1.02.

EXAMPLE XI

A test of the possibility of using i-NOPY-Gly-OSu (8b) for introducing glycine residues into proteins or polypeptides was performed by using lysozyme as the substrate. There are seven free amino functions in lysozyme that might be subject to reaction with 8b. These are located on the six lysine residues, one of which is the N terminal.

To a solution of lysozyme in an aqueous 6M guanidine hydrochloride solution was added compound 8b (dissolved in a small volume of acetonitrile) in a 5:1 molar excess over protein amino functions. The pH of the solution was adjusted to 8–9, and the mixture was stirred at room temperature for 2 hours.

The modified protein isolated after this treatment was subjected to amino acid analysis, the result of which indicated that 4.8 additional glycine residues had been introduced per lysozyme molecule (total glycine content was increased from 12 to 16.8).

The i-NOPY groups were removed from the modified protein by brief treatment with ammonium hydroxide at room temperature to verify this result, since the resulting deblocked glycylated lysozyme could be treated with excess 2,4-dinitrofluorobenzene (DNFB) to determine how many of the lysine residues were protected from reaction as a result of the presence of attached glycine residues. After complete acid hydrolysis of the DNFB-treated glycylated lysozyme, amino acid analysis of such samples indicated that from 4.8 to 5.9 of the six original lysines (Table I) had escaped reaction with DNFB under conditions which, in a control experiment with unmodified lysozyme, caused reaction of DNFB with 5.9 of the 6 lysine residues.

i-NOPY-Glycylation of Lysozme. To a solution of 120 mg of lysozyme (Sigma) in 2.2 mL of 6M guanidine hydrochloride was added 85 mg of 8b in 0.2 mL of acetonitrile. The mixture was made alkaline (pH 8–9) by addition of 0.03 mL of N,N,N',N'-tetramethylethylenediamine (TMEDA) and stirred at room temperature for 2 h and then acidified to pH 2 by addition of 6N hydrochloric acid. Additional water was added (ca. 12 mL), and the precipitate of modified lysozyme was centifuged down and then washed twice with 10 mL of water, three times with 10 mL of warm absolute ethanol, and once with 10 mL of acetonitrile. The final ethanol and acetonitrile supernatants did not show the presence of the N-NOPY chromophore ($\lambda_{max}$ 380 nm), indicating that excess N-NOPY-Gly containing reagent had been removed. The resulting modified lysozyme was obtained in the form of a tan powder. The material gave an ultraviolet spectrum in acetic acid-water (1:1 v/v) in which the absorbance of 0.9 at 380 nm from the N-NOPY-glycine residue exceeded that at 280 nm (0.7). Amino acid analysis of this material gave the results expected for lysozyme, except for an increased amount of glycine amounting to 4.8 residues.

Deblocking of a 23 mg. sample of this N-(i-NOPY)-glycylated lysozyme was carried out by suspending the material in a solution prepared from 2 mL of water, 2 mL of DMF, and 2 mL of concentrated ammonium hydroxide and stirring the mixture for 64 h. A small amount of solid that remained undissolved was centrifuged down. The ultraviolet spectrum of a sample of the supernatant solution diluted with ethanol indicated that it contained the deblocking product, i-NOPY-NH$_2$ ($\lambda_{max}$ 355 nm). The residue obtained by evaporation of the supernatant was combined with the very small centrifuged pellet and mixed with a solution containing 6 mL of water, 6 mL of DMF, and 5 drops of 2,4-dinitrofluorobenzene (DNFB). The mixture was adjusted to a pH of 8–9 by addition of 6 drops of TMEDA and stirred overnight. Concentrated ammonium hydroxide (2 mL) was added to destroy any remaining DNFB and stirring was continued for 2 h. The mixture was dialyzed against distilled water (1 L) for ca. 2 h with two changes of water and then for 64 h. with two additional changes. Samples of the resulting solution of DNFB-treated glycylated lysozyme were taken for amino acid analysis. Results of amino acid analysis are recorded in Table 1.

TABLE 1

Recovery of Glycine and Lysine from Acid-Hydrolyzed NOPY—Gly-Modified and DNP-Modified Lysozyme

| | lysozyme (lit.) | NOPY Gly Lysozyme | DNP Lysozyme | DNP— Gly Lysozyme |
|---|---|---|---|---|
| glycine | 12 | 16.8 | 11.3 | 12.2 |
| lysine | 6 | 5.8 | 0.2 | 5.9 |

It was evident that the active ester 8b is an effective glycylating agent for use in water-containing solvent systems suitable for at least some proteins or polypeptides.

What is claimed is:

1. The compound having the formula

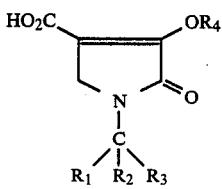

where R$_1$, R$_2$ and R$_3$ are alkyl groups having 1–4 carbon atoms or hydrogen and R$_4$ is an alkyl group having 1–4 carbon atoms.

2. The compound having the formula

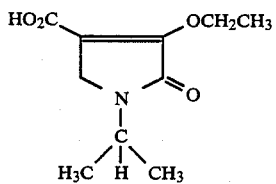

3. The compound having the formula

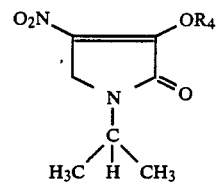

where R$_1$, R$_2$ and R$_3$ are alkyl groups having 1–4 carbon atoms or hydrogen and R$_4$ is an alkyl group having 1–4 carbon atoms.

4. The compound having formula

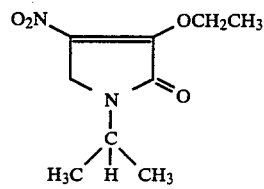

5. The compound having the formula

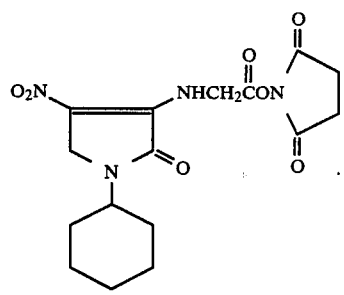

6. The compound having the formula

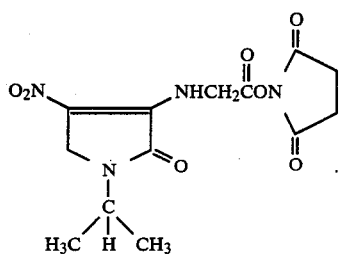

7. The compound having the formula

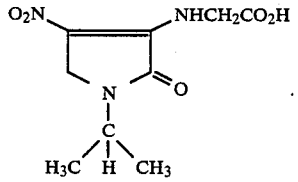

* * * * *